United States Patent
Blaney et al.

[11] Patent Number: 5,662,808
[45] Date of Patent: Sep. 2, 1997

[54] PROCESS AND ARTICLE FOR DISINFECTING WATER

[75] Inventors: Carol Ann Blaney, Roswell; Kristi Lynn Kiick-Fischer, Alpharetta; Rosann Marie Kaylor, Cumming, all of Ga.

[73] Assignee: Kimberly-Clark Worldwide, Inc., Neenah, Wis.

[21] Appl. No.: 678,131

[22] Filed: Jul. 11, 1996

Related U.S. Application Data

[62] Division of Ser. No. 368,833, Dec. 15, 1994, Pat. No. 5,538,629.

[51] Int. Cl.⁶ .................................................. C02F 1/50
[52] U.S. Cl. ................... 210/749; 210/764; 210/753; 210/663; 210/911; 210/912; 210/914
[58] Field of Search ............................ 210/749, 764, 210/753, 663, 911, 912, 914

[56] References Cited

U.S. PATENT DOCUMENTS

| | | | |
|---|---|---|---|
| 4,039,444 | 8/1977 | Bory et al. | 210/36 |
| 4,389,311 | 6/1983 | LaFreniere | 210/198.1 |
| 4,505,823 | 3/1985 | Klein | 210/668 |
| 4,707,263 | 11/1987 | Nishimori et al. | 210/484 |
| 5,217,626 | 6/1993 | Yahya et al. | 210/764 |

FOREIGN PATENT DOCUMENTS

| | | |
|---|---|---|
| 3302073A | 8/1977 | Germany . |
| 3819000A | 12/1989 | Germany . |
| 2-139086A | 5/1990 | Japan . |
| 4-156992A | 5/1992 | Japan . |

OTHER PUBLICATIONS

Trade literature accompanying AccuFilter™ "The Straw", AccuFilter International, Inc., Beaverton, OR.
Trade literature accompanying Potable Aqua® Drinking Water Germicidal Tablets, Wisconsin Pharmacal Co., Inc., Jackson, WI.
The Pur Explorer, *Outside* Magazine, Aug. 1994, p. 117.
Skoog, West & Holler, *Fundamentals of Analytical Chemistry*, 5th ed., Saunders College Publishing, Fort Worth, TX, 1988, p. 780.

*Primary Examiner*—Neil McCarthy
*Attorney, Agent, or Firm*—Joseph P. Harps

[57] ABSTRACT

Disclosed is a process for disinfecting water which provides a visual indication after the disinfection is complete. First, the water to be disinfected is generally simultaneously intermixed with at least three items. The items are: (1) a disinfectant which is adapted to render harmless substantially all pathogens present in the water upon the disinfectant being intermixed with the water for a time period $T_k$; (2) a colorant; and (3) a material which can remove substantially all of the disinfectant and colorant from the water over a time period $T_r$, where $T_r$ is greater than $T_k$. Secondly, the water, disinfectant, colorant and the removing material are allowed to remain intermixed for a time period of $T_r$ or greater. At the end of the time period $T_r$, substantially all pathogens in the water will be rendered harmless, substantially all of the disinfectant will be removed from the water and substantially all of the colorant will be removed from the water. As a result of the removal of the colorant, the water will become uncolored which will give the consumer a visual indication after the disinfection process is complete and the water is safe to drink. Articles for use in carrying out the process are also disclosed.

15 Claims, 4 Drawing Sheets

PROCESS AND ARTICLE FOR DISINFECTING WATER

This application is a divisional of application Ser. No. 08/368,833 entitled "Process and Article For Treating Water" and filed in the U.S. Patent and Trademark Office on Dec. 15, 1994, now U.S. Pat. No. 5,538,629. The entirety of this application is hereby incorporated by reference.

FIELD OF THE INVENTION

The field of the present invention is that of water purification. Purification is broadly interpreted to include disinfection or removal of harmful contaminants or both.

BACKGROUND OF THE INVENTION

Due to the worldwide growth in population and industrialization, along with natural disasters, world supplies of safe drinking water are dwindling. Key pollutants that pose a threat to humans via polluted water consumption are, pathogens (bacteria and viruses), organics, halogenated organics and heavy metals. Conventional water filters are commonly used in American households to remove water impurities and to provide cleaner, more aesthetically pleasing drinking water. However, there are numerous limitations that make these systems difficult to use. They are expensive, bulky, difficult to install and replace, can harbor growth of harmful organisms, are inconvenient, and none claim to remove or kill 100 percent of all pathogens, although most are effective in removing some organics (including halogenated organics) as well as some heavy metals.

Small disposable filters such as those sold under the trade designation Brita®, are expensive by world standards. They can also be somewhat cumbersome to use. A distinct drawback to these types of filtration devices is that they are designed for use in water which is microbiologically safe. That is, the devices are not designed to remove pathogens because it is assumed that the water is pathogen free. Additionally, these devices have only limited utility in the removal of harmful substances such as, for example, heavy metals.

It is difficult for many people in the world, including world travelers, to obtain safe drinking water without having to endure the inconvenience of disinfecting it by either boiling it or through the use of iodine-based disinfectants. In many locales, iodine-based disinfectants are not readily available. When available, it is well known that some of the iodine-based disinfectant systems currently being deployed leave a distinctively bad taste in the mouth. Additionally, due to the fact that the iodine is consumed, potentially adverse medical effects can arise, especially for individuals having thyroid problems. In any event, these methods do nothing to remove metals and organics.

Some of the presently available iodine-based products for the disinfection of water for drinking purposes have overcome the potential medical difficulties which may present themselves due to the consumption of iodine. One such product is manufactured by AccuFilter International, Inc. under the trade designation "THE STRAW". This device is an opaque tubular object which is inserted into the water to be disinfected. At the base of the tube, on the inside, is a disinfecting medium of iodine. Further up the tube, on the inside, is a matrix of activated carbon. In use, the base of the tube is inserted into the water to be disinfected and the consumer sucks on the other end thereby pulling the water through the iodine medium and, thereafter, through the matrix of activated carbon. As the water passes through the iodine medium, it is disinfected. Thereafter, as the iodine-loaded water is passed through the matrix of activated carbon, substantially all of the iodine is removed. The manufacturer states that water sucked out of "The Straw" will be disinfected and substantially free of iodine. A warning to those individuals having thyroid problems is present. They are instructed to consult their doctor prior to using the device.

Another presently available device is manufactured by Recovery Engineering Inc. under the trade designation "The Pur Explorer". This device is a canister having a plunger arrangement which can force water through an iodine-based disinfectant to achieve potability of the water. A product review in the August, 1994 issue of "Outside" magazine states that the Pur Explorer is certified by the EPA to deactivate all types of waterborne infectious agents, including viruses. This is achieved by passing the water through an iodine matrix during the filtration process. It is also stated that an optional carbon cartridge removes the small amount of iodine from the filtered water.

Yet another presently available commercial system is marketed under the trade designation POTABLE AQUA® WITH P.A. PLUS by Wisconsin Pharmacal Co., Inc. of Jackson, Wis. Two separate tablets which are separately and sequentially added to water to be purified are involved in this system. First, a POTABLE AQUA® tablet is added to one quart of water to be purified. (Two tablets are to be used if contamination of the water with Giardia is suspected.) The active ingredient of the tablet is tetraglycine hydroperiodide (16.7%). That is, each tablet contains 6.68% of titratable iodine. The POTABLE AQUA® tablet is allowed to dissolve in the water for ten (10) minutes. (Twenty minutes are recommended if Giardia is suspected.) At this point, the water is faintly colored orange. Thereafter, one P.A. PLUS tablet is added to the quart of water in order to neutralize the iodine taste instilled in the water by the POTABLE AQUA® tablet. The active ingredient in the P.A. PLUS tablet is ascorbic acid. Each P.A. PLUS tablet contains 45 milligrams (mg) of ascorbic acid. After addition of the P.A. PLUS tablet the container is shaken and three (3) minutes are allowed to pass. Thereafter, the water turns clear in color and is drinkable. Importantly, the literature accompanying the system states that the POTABLE AQUA® tablet and the P.A. PLUS tablet must not be added to the water at the same time. Also stated is that adding the P.A. PLUS tablet before the expiration of the twenty minute period may allow harmful organisms to remain in the water. Clearly, this system involves the sequential addition of the two tablets.

While all of these devices do address the problems associated with the bad taste of iodine-based disinfectants and the concomitant medical problems which may be associated with the ingestion of large amounts of iodine, none of these products offer the consumer a single step product which gives a reliable visual indication after the disinfection process has been completed and the water is safe to drink. In particular, while the POTABLE AQUA® WITH P.A. PLUS does provide a visual indication, the indication is not that the water has been purified, but rather that the iodine present due to the predetermined, timed, first step has been removed. In other words, a consumer utilizing either of these products must take it on faith that the product has performed satisfactorily and the water is, in fact, safe to drink. Importantly, with the POTABLE AQUA® WITH P.A. PLUS system, the consumer without independent timing mechanisms such as a watch is at a distinct disadvantage in determining the point in time that the water is safe to drink.

From the above, it is clear that there exists a distinct need for a one-step process and article which allows a consumer to disinfect or otherwise purify water without having to resort to an independent timing mechanism. That is, there is a distinct need for a process and article which provides a visual indication after the purification process is complete and the water is safe to drink.

OBJECTS OF THE INVENTION

It is a general object of the present invention to provide a process for obtaining disinfected drinking water which provides a visual indication to the consumer after the disinfection process has been completed and the water is safe to drink.

It is another general object of the present invention to provide an article capable of disinfecting water which gives the consumer a visual indication after the water has, in fact, been disinfected and is safe to drink.

These and other objects and the broad scope of applicability of the present invention, will become apparent to those of skill in the art from the details given hereinafter. However, it should be understood that the detailed description of the presently preferred embodiments of the present invention is given only by way of illustration because various changes and modifications well within the spirit and scope of the invention will become apparent to those of skill in the art in view of this detailed description.

SUMMARY OF THE INVENTION

In response to the foregoing difficulties encountered by those of skill in the art, we have discovered a process for disinfecting water which provides a visual indication after the disinfection is complete. First, the water to be disinfected is generally simultaneously intermixed with at least three items. The items are: (1) a disinfectant which is adapted to render harmless substantially all pathogens present in the water upon the disinfectant being intermixed with the water for a time period $T_k$; (2) a colorant; and (3) a material which can remove substantially all of the disinfectant and colorant from the water over a time period $T_r$, where $T_r$ is greater than $T_k$. Inclusion of the colorant, naturally, colors the water and gives an indication that the disinfection process has begun. Of course, the presence of the colorant does not indicate the presence or absence of pathogens. Secondly, the water, disinfectant, colorant and the removing material are allowed to remain intermixed for a time period of $T_r$ or greater. At the end of the time period $T_r$, substantially all pathogens in the water will be rendered harmless, substantially all of the disinfectant will be removed from the water, and substantially all of the colorant will be removed from the water. As a result of the removal of the colorant, the water will become uncolored which will give the consumer a visual indication after the disinfection process is complete and the water is safe to drink. In other words, the consumer will not have to keep track of the time necessary to achieve disinfection because the water will remain visibly colored until the time period $T_r$ has passed. Because $T_r$ is greater than $T_k$, the water will have been disinfected when the colorant is removed.

In some embodiments, the disinfectant may be selected from the group including one or more of iodine, halazone, phenols or quaternary ammonium compounds. If the disinfectant is iodine, the disinfectant may be an iodine compound such as tetraglycine hydroperiodide or colloidal iodine.

In some embodiments, the colorant may be selected from the group including one or more of iodine, edible colorants or gape tannins. Accordingly, in some embodiments one material may serve the dual purpose of disinfectant and colorant. One material which serves both of these purposes is iodine. Alternatively, the colorant may be a food grade colorant. For example, the colorant may be FD&C Blue #1 or FD&C Red #40.

In some embodiments, the material which is adapted to remove the disinfectant and colorant may be selected from the group including one or more of activated carbon, zeolites or clays.

Exemplary pathogens which may be targeted for destruction include one or more pathogens selected from the group including vibrio choleras, giardia lamblia, cryptosporidium, salmonella, fecal coliforms, reovirsus, adenoviruses and human enteric viruses such as polio, hepatitis A and coxsackie.

In some embodiments, the process may include the additional step of treating the water during the time of disinfection in some manner.

For example, the treatment may include adding substances to the water which are useful for, for example, promoting good health or enhancing the colorant. Alternatively, the treatment may be directed toward the removal of substances other than the disinfectant and colorant where the substances to be removed are harmful.

If a substance is to be added by the treating step, the substance may be selected from the group including water-soluble vitamins, minerals, trace nutrients and colorant enhancers. Exemplary water-soluble vitamins which may be added include one or more vitamins selected from the group including B vitamins and vitamin C. Exemplary minerals which may be added include one or more minerals selected from the group including calcium, magnesium, potassium, sodium, iron or phosphorous. Exemplary trace nutrients which may be added include one or more trace nutrients selected from the group including zinc or copper. An exemplary colorant enhancer is starch.

If a substance is to be removed by the treating step, the substance may be selected from the group including heavy metals, organics, halogenated organics, polyaromatics, and halogenated polyaromatics. It is particularly desirable to remove pesticides and herbicides where they are present as a result of run-off contamination. Exemplary heavy metals which may be removed by the treating step include lead, nickel, mercury, copper and arsenic.

The present invention is also directed toward an article for disinfecting water and whose use provides a visual indication after a time period sufficient for the disinfection to be complete. The article includes: (1) a disinfectant adapted, when the article is placed in contact with the water, to render harmless substantially all pathogens contained in the water after a time period $T_k$; (2) a colorant; and (3) a material adapted, when the article is placed in contact with the water, to remove substantially all of the disinfectant and colorant from the water over a time period $T_r$, where $T_r$ is greater than $T_k$.

In some embodiments the article will further include a treating material which is adapted to treat water with which the article comes in contact by either adding or removing one or more substances. In some embodiments the treating material may be adapted to both add substances and remove different substances.

In one embodiment the article includes a bag formed from a water-pervious material. The bag defines at least one interior chamber which contains: (1) a disinfectant adapted, when the bag is immersed in the water, to render harmless substantially all pathogens contained in the water after a time period $T_k$; (2) a colorant; and (3) a material adapted, when the bag is immersed in the water, to remove substantially all of the disinfectant and colorant from the water over a time period $T_r$, where $T_r$ is greater than $T_k$.

In some embodiments the chamber will further include a treating material which is adapted to treat water, with which the article comes in contact, by either adding or removing one or more substances. In some embodiments the treating material may be adapted to both add substances and remove different substances. Of course, the bag may define a plurality of chambers with each of the chambers containing one or more of the components of the article. For example, the bag could include two cheers with the disinfectant in a first chamber and the colorant and the removing material being located in a second chamber. Naturally, embodiments involving more than two chambers are envisioned.

In some embodiments the water-pervious bag material may be formed from a material selected from the group including abaca pulp or rayon.

DETAILED DESCRIPTION OF THE INVENTION

The present invention can be utilized in a wide variety of embodiments. Only a few of these embodiments, including the best mode of the invention presently contemplated will be detailed herein. Generally speaking, the present invention is directed toward a single-use, disposable product and process which provides the user with disinfected water and also provides the user with a visual indication after the disinfection process has been completed and the water is safe to drink. Exemplary pathogens which may be targeted for destruction include one or more pathogens selected from the group including vibrio cholerae, giardia lamblia, cryptosporidium, salmonella, fecal coliforms, reovirus, adenoviruses and human enteric viruses such as polio, hepatitis A and coxsackie.

Figure 1:
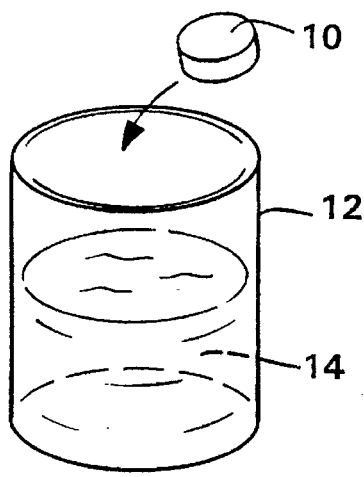

Turning now to the figures where like reference numerals designate like elements or process steps, and, in particular, to FIG. 1, a first embodiment, of the present invention is illustrated in a disk-like or cookie-like shaped form 10. The disk 10 is placed into a container 12 of water 14 which is to be disinfected.

The disk 10 is formed from a mixture of ingredients which include: (1) a water-soluble disinfectant adapted, when the article is placed in contact with the water 14, to render harmless substantially all pathogens contained in the water 14 after a time period $T_k$; (2) a colorant; and (3) a material adapted, when the article is placed in contact with the water 14, to remove substantially all of the disinfectant and colorant from the water 14 over a time period $T_r$, where $T_r$ is greater than $T_k$. Because the amount of disinfectant, colorant and removing material will vary with the amount of water 14 contained in the container 12, different sizes of disks 10 can be prepared and labeled as to the maximum amount of water 14 with which they can be satisfactorily used. It is also envisioned that the disk 10 may include inert ingredients such as conventional fillers and binders which enable the first three ingredients to be formed into the disk form. The composition of the disk 10 is engineered so that the disk 10 will rapidly disintegrate into small particles when the disk 10 is placed in water 14 and subjected to light agitation.

Those of skill in the art will readily recognize that a wide variety of disinfectants may be utilized in the present invention. For example, the disinfectant may be selected from the group including one or more of iodine, iodine compounds such as tetraglycine hydroperiodide, halazone, phenols or quaternary ammonium compounds.

In like manner, a wide variety of colorants may be utilized in the present invention. For example, the colorant may be selected from the group including one or more of iodine, edible colorants or grape tannins. Alternatively, the colorant may be a food grade colorant. For example, the colorant may be obtained under the designation FD&C Blue #1 or FD&C Red #40.

Likewise, the "removing material", that is the material which is adapted to remove the disinfectant and colorant, may be selected from any conventional material which will absorb, adsorb or otherwise neutralize the disinfectant and the colorant. That is, the removing material may be an adsorbent, an absorbent or a neutralizing agent. If for example, the removing material is an adsorbent, it may be selected from the group including one or more of activated carbon, zeolites or clays. If the removing material is a neutralizing agent, it may be selected from the group including ascorbic acid and sodium thiosulfate.

It should be readily apparent to those of skill in the art that, in some embodiments, one material may serve dual purposes. For example, one material may serve the purpose of both disinfectant and colorant. One material which serves both of these purposes is iodine.

Next, the water 14 in the container 12 is gently agitated for several minutes in order to achieve disintegration of the disk 10 into numerous small particulates and to thoroughly intermix the particulates throughout the water 14. Naturally, this action will result in a good distribution of the disinfectant, colorant and removing material throughout the water 14 sample. Distribution of the colorant throughout the water 14 sample, will result in the water 14 becoming colored.

The disk 10 will be designed to contain enough water-soluble disinfectant to adequately disinfect a given maximum quantity of water in a fairly short time period($T_k$). These quantities are well known to those of skill in the art. For example, it is known that a concentration of $I_2$ of 2 parts per million (ppm) will disinfect water in approximately forty (40) minutes and that a concentration of 4 ppm $I_2$ will disinfect water in approximately twenty (20) minutes. Additionally, the amount of colorant present will be selected so that the removing material will not remove substantially all of the colorant until time period ($T_r$) which is longer than $T_k$. As a result of this arrangement, the water 14 will remain colored until such time that it has been completely disinfected. Therefore, the user/consumer will be given a visual indication after the disinfecting process is complete by the colorant being removed from the water 14.

Of course, during the time that the disinfection of the water is taking place, the removing material is also removing the disinfectant. That is, the removing material is performing the dual function of removing the colorant and the disinfectant within the time period $T_r$.

Figure 2:
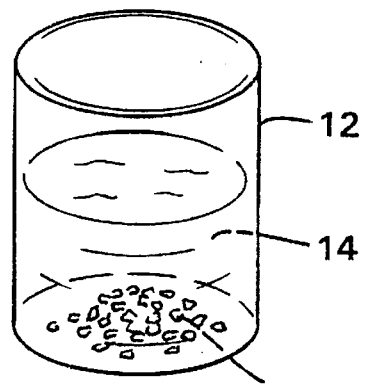

Turning to FIG. 2, once the colorant has been removed from the water 14, the user/consumer can wait until the particles 16 of the disk 10 settle to the bottom of the container 12 to drink the water 14. Alternatively, the disinfected water 14 could be decanted off the top into a drinking glass or passed through a filtration device to remove the particles 16. Since no disinfectant remains, however, the disinfected water is susceptible to recontamination and so should be consumed within several hours.

Figure 3:
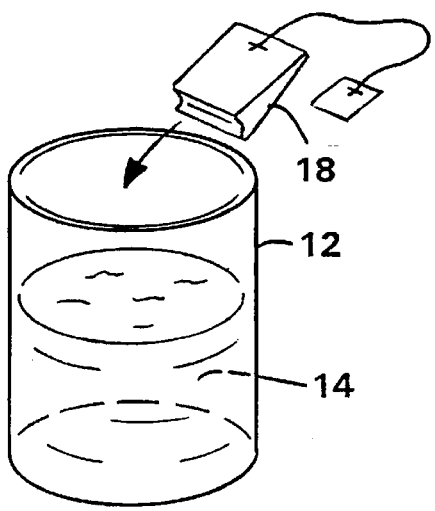
Figure 4:
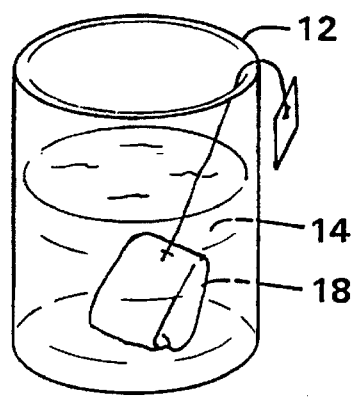

FIG. 3 illustrates a second embodiment of the present invention which operates in substantially the same fashion as that depicted in FIGS. 1 and 2. The embodiment of FIG. 3 varies from that of FIGS. 1 and 2 in that the disinfectant, colorant and removing material are contained in a small pouch 18 formed from a water-pervious, hydrophilic material. The pouch is equivalent to a conventional tea bag in construction and function in that it is water-pervious. The mode of operation of this embodiment is essentially the same as that of the disk 10 with the exception that all of the materials of the disinfection process can be readily removed from the water 14 upon completion of the disinfection process. The water 14 is, in this embodiment, disinfected substantially like tea is brewed with the exception that external heat is not necessary and the disinfectant and colorant are readsorbed or neutralized as the case may be. That is, the pouch 18 is dipped into a container 12 of water 14 which is to be disinfected, the water 14 is slightly agitated to facilitate intermixing and the pouch 18 is removed upon the colorant being removed from the water 14. FIG. 4 illustrates the pouch 18 in use.

In some embodiments, some of the components may be contained within (that is incorporated into) the water-pervious, hydrophilic material so that these components will be near the surface of the pouch 18 and will be able to more readily escape into the water. In these embodiments, the removing material would still be contained within the pouch 18. Containment of the removing material within the pouch 18 while incorporating some or all of the other components into the water-pervious material allows the other components a "head start" on the removing material. That is to say, the other components will be able to disperse throughout the water to a greater degree and thereby perform their intended function before coming into contact with the removing material. Inclusion of the disinfecting agent in the water-pervious material allows the disinfecting agent to more rapidly increase in concentration prior to commencement of the action of the removing material. In such an embodiment, more rapid disinfection will likely occur as a result of the higher initial concentration of disinfecting agent in the water.

In yet other embodiments, where it is believed that the water to be consumed does not harbor any harmful pathogens but does, in fact, harbor one or more harmful substances, the present invention is directed to a pouch 18 which does not contain disinfectant. That is the pouch 18 contains only the appropriate removing material or the removing material along with any desired treating materials.

Figure 5:
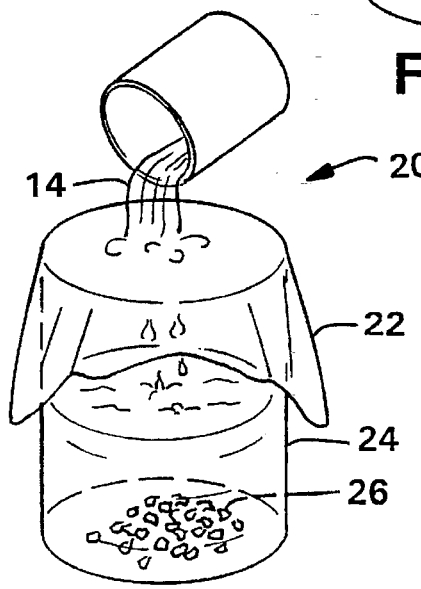

FIG. 5 illustrates yet a further embodiment of the present invention. For example, FIG. 5 illustrates an article 20 adapted for the disinfection process which includes a fabric 22 which contains entrapped disinfectant and colorant. The article 20 also includes a container 24 having the removing material 26 attached to the inside of the container 24 in an immobilized fashion. In use, the water 14 to be disinfected is passed through the fabric 22 whereby the disinfectant and colorant are intermixed therewith. The removing material 26 which is located on the inside of the container, for example, on the bottom as illustrated in FIG. 5, thereafter removes the disinfectant and colorant from the water 14.

Of course, it should be realized that, in some simple embodiments, all three ingredients can simply be contained within an open-mouthed pouch with the contents being dumped into a container of water when it is desired to disinfect the water. Thereafter, the pouch can be disposed of or reloaded with an appropriate amount of the three materials. In one embodiment, the pouch could be used as a filtration device to separate the water from the remains of the removing material.

Those of skill in the art will readily recognize that a large number of variations and modifications to the present invention can be made. For example, the process may include the additional step of treating the water during the time of disinfection in some manner. If such is the case, the article for achieving the disinfection of the water must be modified accordingly.

In this regard, the treatment may add substances to the water which are useful, for example, in promoting good health and/or enhancing the colorant. Alternatively, the treatment may be directed toward the removal of substances other than the disinfectant and colorant where the substances to be removed are potentially harmful if ingested. That is organics, heavy metals, halogenated organics, polyaromatics, halogenated polyaromatics, pesticides, herbicides and the like.

If it is desired to add a substance, the substance to be added need only be added as an additional component of the article (disk, tea bag, etc.) in a form which is water-soluble. Thus, when the article comes into contact with the water during the disinfecting process, the substance to be added will dissolve into the water and be ingested by the consumer. Of course, care needs to be taken to make sure that the removing material does not remove the added substance to any great extent. If a substance is to be added by the treating step, the substance may be selected from the group including water-soluble vitamins, minerals, trace nutrients and colorant enhancers. Exemplary water-soluble vitamins which may be added include one or more vitamins selected from the group including B vitamins and vitamin C. Exemplary minerals which may be added include one or more minerals selected from the group including calcium, magnesium, potassium, sodium, iron or phosphorous. Exemplary trace nutrients which may be added include one or more trace nutrients selected from the group including zinc or copper. An exemplary colorant enhancer is starch. Starch is a colorant enhancer when the colorant is iodine. The presence of starch in the water to be disinfected or otherwise purified, greatly magnifies the intensity of color present as a result of iodine being present. At low concentrations of iodine, the water may appear to be color-free even though trace amounts of iodine are, in fact, presence. Addition of starch magnifies and increases the color to a level detectable by normal eye sight. Naturally, different materials may be utilized to enhance iodine or, for that matter, of other colorants.

If a substance is to be removed by the treating step, the removing material present to remove the disinfectant and the colorant may also be effective in removing additional substances. Alternatively, if it is desired to remove an additional substance which the removing material does not effectively remove by, for example, absorption, adsorption or neutralization, additional different removing material(s) may be added which specifically target such additional substance(s).

If a substance is to be removed by the treating step, the substance may be selected from the group including heavy metals, organics, halogenated organics, polyaromatics, and halogenated polyaromatics. It is particularly desirable to remove pesticides and herbicides where they are present as a result of run-off contamination. Exemplary heavy metals which may be removed by the treating step include lead, nickel, mercury, copper and arsenic.

Other additives may include binders, selected vitamins, minerals and/or flavors. During the several minutes that the water is gently stirred, the disinfectant kills bacteria and viruses while the solid sorbent adsorbs organics, including halogenated organics. Heavy metals may also be adsorbed if an appropriate solid sorbent is chosen. The solid sorbent also serves to remove, by adsorption, the residual disinfectant and any color indicator if present. The color indicator's disappearance (at the point when the water appears clear) indicates that substantially all the germs have been killed, substantially all disinfectant has been adsorbed or neutralized, and substantially all organic contaminants have been removed. The water may be stored with or without the solid particles for many hours before consuming. The article may also release calcium, magnesium, vitamin C or any other chosen healthful vitamins or minerals or flavors at appropriate times in the cycle via a controlled release mechanism or other mechanism.

Those of skill in the art will recognize that the sequencing of the release of the disinfectant, colorant, removing material and treating material, if present, can be engineered as desired. For example, the removing material and/or treating material may be encapsulated within a substance which slowly dissolves in water so that the removing material and/or treating material is exposed to the water in a predetermined timed fashion depending upon the thickness of the encapsulating coating. In particular, the disinfectant and colorant could first be released to indicate to the consumer that the disinfecting process was under way. Release of the removing material would be delayed until such time as the disinfectant has achieved the concentration desired. If present, release of treating materials that are additives could be delayed until a time shortly prior to the colorant being absorbed or neutralized by the removing material. This would lessen the likelihood of the removing material also removing the additive.

For example, the activity of the removing material can be delayed by encapsulating or coating the removing material with a water-soluble material which slowly dissolves over time. Upon dissolution of the coating, the removing material will begin to remove the disinfectant. This embodiment allows the disinfectant a period of time to achieve the concentration necessary for disinfection prior to it being removed by the removing material.

EXPERIMENTATION

A first experiment, experiment number 1, was conducted to demonstrate that activated carbon contained in a water-pervious pouch can remove iodine from a sample of water within a time period sufficiently short to make the present invention commercially viable.

Figure 6:
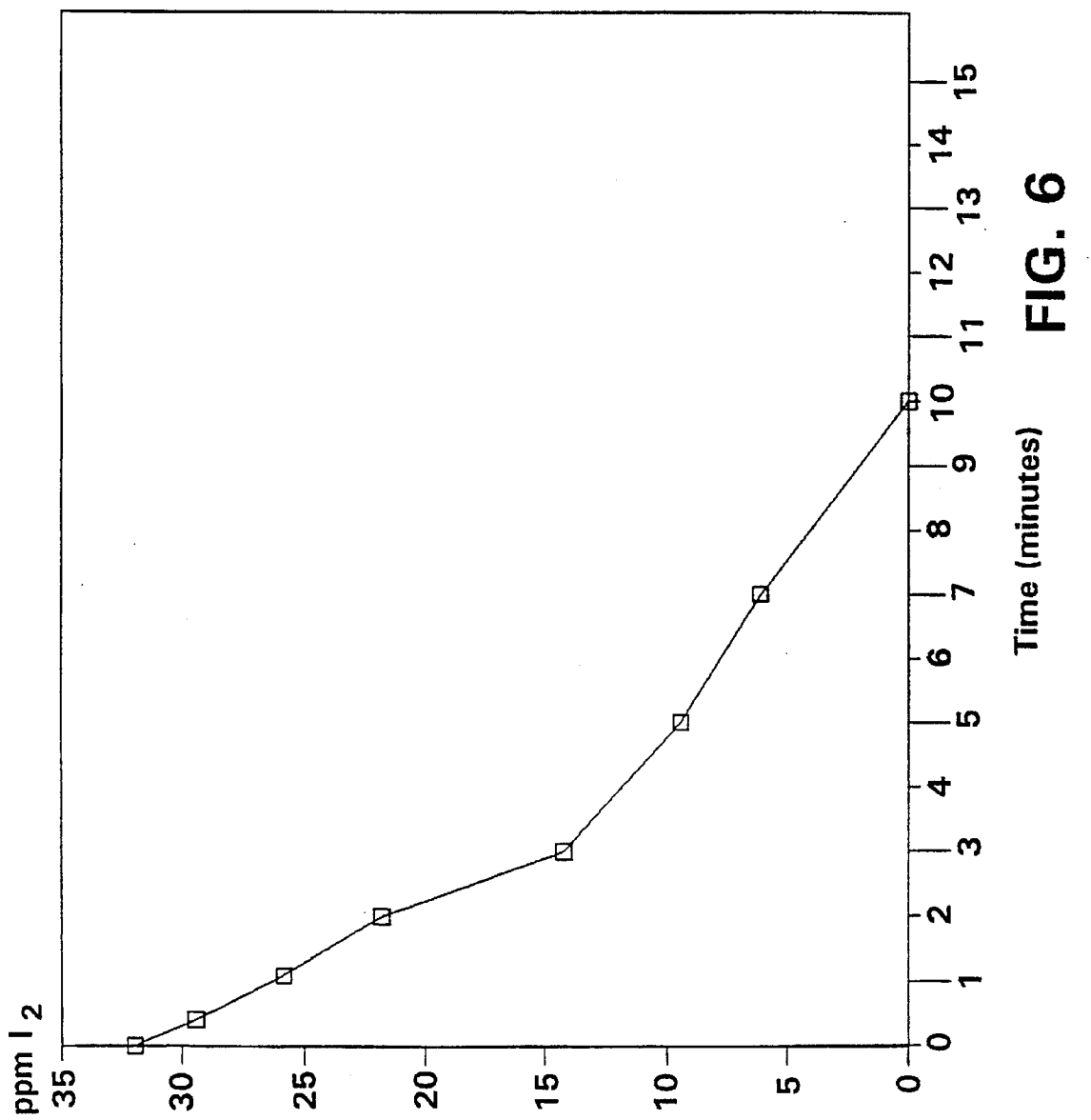

Five six-inch square pouches were made of heat-sealable tea bag paper having a basis weight of about sixteen grams per square meter (21 gsm) manufactured by the Kimberly-Clark Corp. of Dallas, Tex. under the trade designation BHS 555. Each pouch was filled with 20 grams of activated carbon manufactured by Calgon Carbon Corp. of Pittsburgh, Pa. under the trade designation F816 (8×16 mesh). The pouches were placed in two (2) liters of distilled water containing about thirty two (32) parts per million (ppm) of iodine. The iodine also acted as a colorant in that the water had a distinct orange color. The water and pouches were then continuously stirred using a stirring rod, and 25 ml aliquots of the water were drawn at the time intervals recited in Table 1. These aliquots were analyzed within three minutes of drawing each sample by the conventional titration procedure recited at page 780 of "Fundamentals of Analytical Chemistry" authored by Skoog, West & Holler, printed by Saunders College Publishing (1988). FIG. 6, which is a graphic depiction of the data in Table 1, demonstrates that the iodine level in the water decreased approximately linearly to less than 0.9 ppm in 10 minutes at which time the water was clear. The sensitivity of the measurement used had a lower limit of 0.9 ppm and a margin or error of ±1 ppm.

TABLE 1

ACTIVATED CARBON/IODINE EXPERIMENT

| Time (min) | Titrant mL $Na_2S_2O_3$ (0.001 M) | Iodine Molarity | Iodine (ppm) |
| --- | --- | --- | --- |
| 0.0 | 6.3 | 0.000126 | 32.0 |
| 0.4 | 5.8 | 0.000116 | 29.4 |
| 1.1 | 5.1 | 0.000102 | 25.9 |
| 2.0 | 4.3 | 0.000086 | 21.8 |
| 3.0 | 2.8 | 0.000056 | 14.2 |
| 5.0 | 1.85 | 0.000037 | 9.4 |
| 7.0 | 1.2 | 0.000024 | 6.1 |
| 10.0 | 0 | 0 | ND |

ND = Not Detected

A second experiment, experiment number 2, was conducted to determine the effect the inclusion of the disinfectant (iodine) within a pouch would have on the concentration of disinfectant present in the water.

Figure 7:
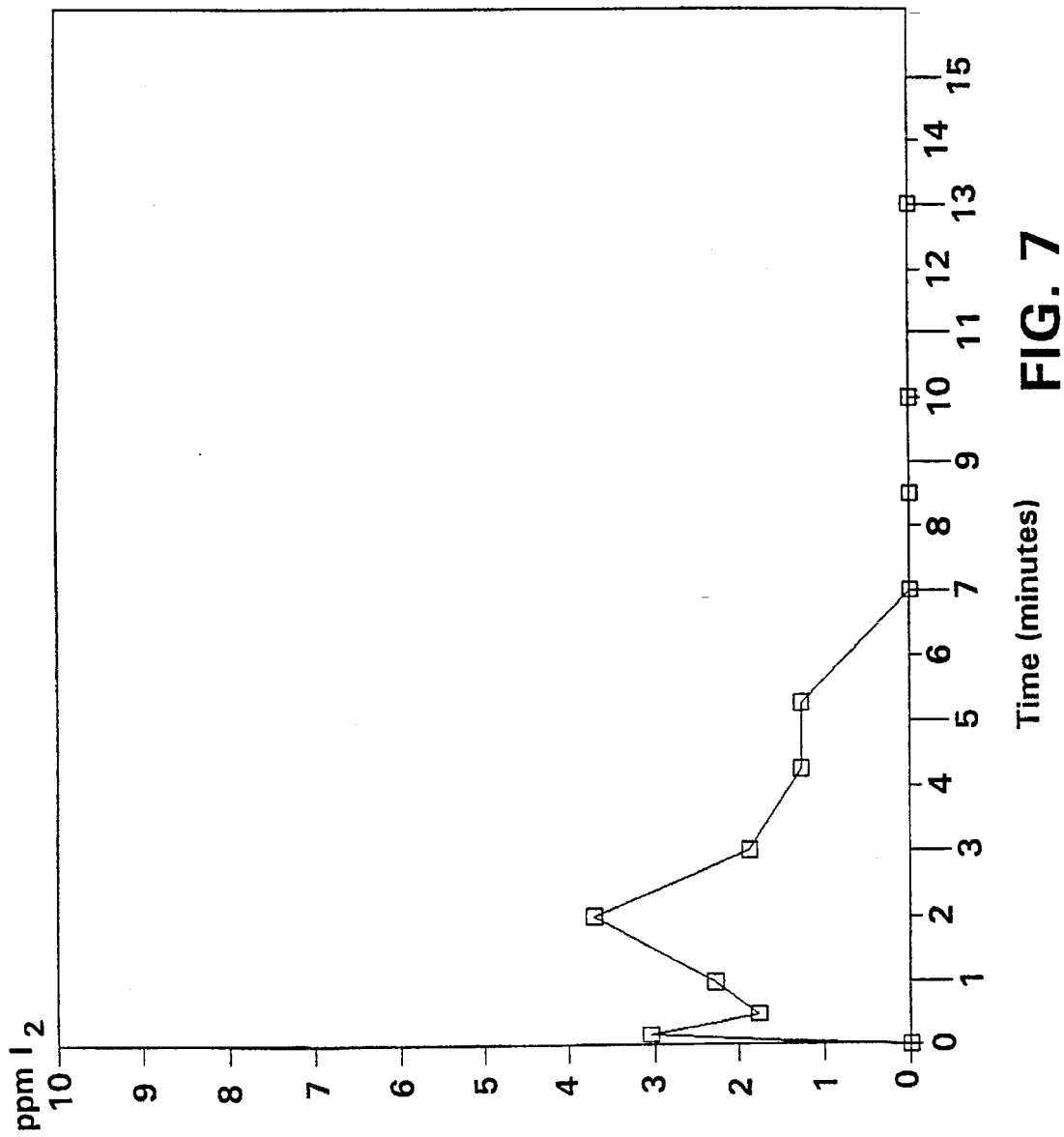

In experiment number 2, two pouches identical to those used in experiment 1, were each filled with fifty grams (50 gms) of activated carbon. Additionally eight (8) germicidal tablets manufactured by Wilson Pharmacal Co., Inc. of Jackson, Wis. under the trade designation POTABLE AQUA® were crushed and added to the pouch. The tablets included 16.7 weight percent of tetraglycine hydroperiodide. Fifty (50) POTABLE AQUA® tablets weigh 0.21 ounces. Accordingly, 0.0056 ounces of tetraglycine hydroperiodide were contained in each pouch. After sealing, the pouches were placed in two (2) liters of distilled, deionized water within five (5) minutes of the crushing of the tablets. The water and pouches were then continuously stirred using a stirring rod, and 25 ml aliquots were drawn at the time intervals recited in Table 2. These aliquots were analyzed within three (3) minutes of drawing each sample, by the titration procedure cited above. Table 2 demonstrates that the iodine level in the water first rose to about 4 ppm in approximately two (2) minutes, and then decreased to below 0.9 ppm in about seven (7) minutes. FIG. 7 is a graphic depiction of Table 2.

TABLE 2

ACTIVATED CARBON/IODINE EXPERIMENT
(Pouches With Tablets and Activated Carbon)

| Time (min) | Titrant mL $Na_2S_2O_3$ (0.001 M) | Iodine Molarity | Iodine (ppm) |
| --- | --- | --- | --- |
| 0 | 0 | 0 | ND |
| 0.2 | 0.6 | 0.000012 | 3.0 |
| 0.5 | 0.35 | 0.000007 | 1.8 |
| 1.0 | 0.45 | 0.000009 | 2.3 |
| 2.0 | 0.73 | 0.0000146 | 3.7 |
| 3.0 | 0.37 | 0.0000074 | 1.9 |
| 4.3 | 0.25 | 0.000005 | 1.3 |
| 5.3 | 0.25 | 0.000005 | 1.3 |
| 7.0 | 0 | 0 | ND |
| 8.5 | 0 | 0 | ND |
| 10 | 0 | 0 | ND |
| 13 | 0 | 0 | ND |

ND = Not Detected

This experiment demonstrated that the presence of the water-pervious pouch material limited the maximum concentration of iodine. In all likelihood, the close proximity of the disinfecting iodine and the recovering material, activated carbon, also played a large part in the lowered maximum concentration of disinfecting iodine. These factors will have to be kept in mind when determining the amount of material to be retained within pouches for commercial application. It is imperative that the iodine concentration be allowed to achieve a level capable of disinfection within the time period the level is maintained before its removal by the removing material.

Figure 8:
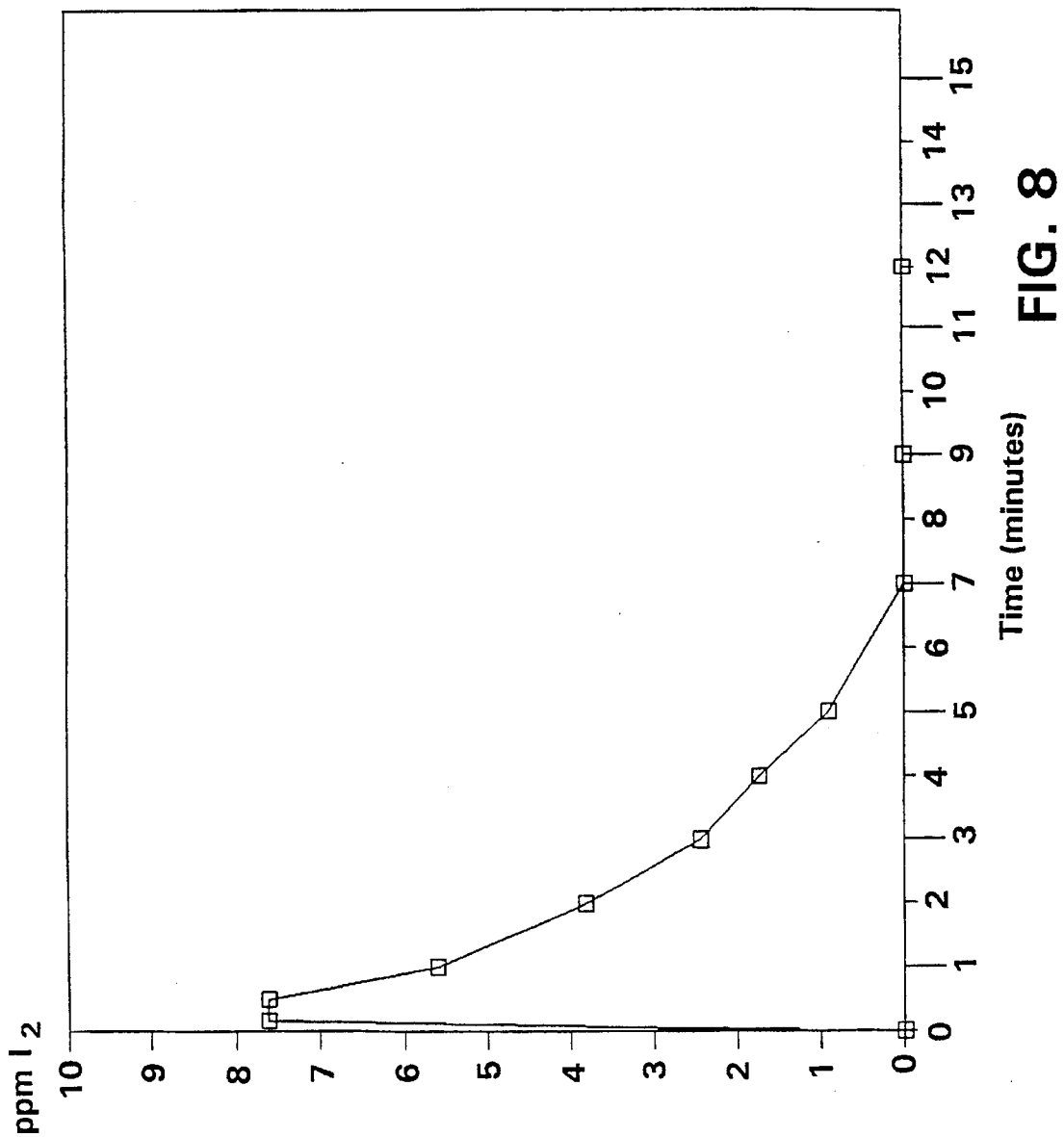

As further evidence of the effect of the pouch material and the close proximity of the disinfectant and the removing material on the maximum iodine concentration achieved, a third experiment, experiment number 3, was conducted. In experiment no. 3, sixteen (16) POTABLE AQUA® tablets described in experiment 2 were crushed, ground and combined with one hundred grams (100 gms) of the activated carbon described in experiment 1. The tablets and charcoal were added to two (2) liters of distilled water within three (3) minutes of the grinding. The water was then continuously stirred using a stirring rod, and 25 ml filtered aliquots were taken at the time intervals recited in Table 3. These aliquots were analyzed within three (3) minutes of drawing each sample, by the titration procedure cited above. The results of this experiment are reported in Table 3 where it is demonstrated that the iodine level in the water first rose to about 8 ppm in one (1) minute, and then decreased approximately linearly to 2.4 ppm in three (3) minutes, and then decreased approximately linearly to less than 0.5 ppm in about seven (7) minutes. FIG. 8 is a graphic depiction of Table 3.

TABLE 3

ACTIVATED CARBON/IODINE EXPERIMENT
(Tablets and Activated carbon)
(No Pouch)

| Time (min) | Titrant mL $Na_2S_2O_3$ (0.001 M) | Iodine Molarity | Iodine (ppm) |
|---|---|---|---|
| 0 | 0 | 0 | ND |
| 0.2 | 1.5 | 0.00003 | 7.6 |
| 0.5 | 1.5 | 0.00003 | 7.6 |
| 1.0 | 1.1 | 0.000022 | 5.6 |
| 2.0 | 0.75 | 0.000015 | 3.8 |
| 3.0 | 0.48 | 0.0000096 | 2.4 |
| 4.0 | 0.34 | 0.0000068 | 1.7 |
| 5.0 | 0.18 | 0.0000036 | 0.9 |
| 7.0 | 0 | 0 | ND |
| 9 | 0 | 0 | ND |
| 12 | 0 | 0 | ND |

ND = Not Detected

A fourth experiment was conducted to demonstrate the rapid rise in iodine concentration achievable with sixteen (16) tablets of POTABLE AQUA® in the absence of any removing material. The sixteen tablets were dissolved in two (2) liters of distilled water. No activated carbon was added. Within two (2) minutes of adding the tablets, the solution was measured to contain 32.7 ppm iodine by the titration procedure cited above. The effects of the pouch material and removing agent are clear.

It is to be understood that variations and modifications of the present invention may be made without departing from the scope of the invention. It is also to be understood that the scope of the present invention is not to be interpreted as limited to the specific embodiments disclosed herein, but only in accordance with the appended claims when read in light of the foregoing disclosure.

What is claimed is:

1. A process for disinfecting water which provides a visual indication after the disinfection is complete, the process including the steps of:

providing water;

intermixing the water with a disinfectant for a time period $T_k$, where $T_k$ is sufficient to allow the disinfectant to render harmless substantially all pathogens present in the water;

intermixing the water with a colorant;

intermixing the water with a material adapted to remove substantially all of the disinfectant and colorant from the water over a time period $T_r$, where $T_r$ is greater than $T_k$;

wherein the water, disinfectant, colorant and material are intermixed for a time period of $T_r$ or greater; and whereby substantially all pathogens in the water are rendered harmless, substantially all of the disinfectant is removed from the water and substantially all of the colorant is removed from the water.

2. The process according to claim 1, wherein the disinfectant is selected from the group consisting of solid iodine, iodine compounds, phenols, halazone or quaternary ammonium compounds.

3. The process according to claim 2, wherein the iodine compound is tetraglycine hydroperiodide.

4. The process according to claim 1, wherein the colorant is selected from the group consisting of iodine, edible colorants or grape tannins.

5. The process according to claim 1, wherein the material which is adapted to remove the disinfectant and colorant is selected from the group consisting of activated carbon, zeolites or clays.

6. The process according to claim 1, wherein the pathogens are selected from the group consisting of vibrio choleras, giardia lamblia, cryptosporidium, salmonella, fecal coliforms, reovirsus, adenoviruses and human enteric viruses such as polio, hepatitis A and coxsackie.

7. A process for disinfecting and treating water which provides a visual indication after the disinfection is complete, the process including the steps of:

providing water;

intermixing the water with a disinfectant for a time period $T_k$, where $T_k$ is sufficient to allow the disinfectant to render harmless substantially all pathogens present in the water;

intermixing the water with a colorant and a treating material;

intermixing the water with a material adapted to remove substantially all of the disinfectant and colorant from the water over a time period $T_r$, where $T_r$ is greater than $T_k$;

wherein the water, disinfectant, colorant and materials are intermixed for a time period of $T_r$ or greater; and whereby substantially all pathogens in the water are rendered harmless, substantially all of the disinfectant is removed from the water, substantially all of the colorant is removed from the water and the water is treated.

8. The process according to claim 7, wherein the treating material is adapted to add at least one substance to the water.

9. The process according to claim 8, wherein the substance is selected from the group consisting of vitamins, minerals, trace nutrients or colorant enhancers.

10. The process according to claim 9, wherein the vitamin is selected from one or more of the group consisting of B vitamins or vitamin C.

11. The process according to claim 9, wherein the mineral is selected from the group consisting of one or more of calcium, magnesium, potassium, sodium, iron or phosphorous.

12. The process according to claim 9, wherein the trace nutrient is selected from the group consisting of one or more of zinc or copper.

13. The process according to claim 7, wherein the treating material is adapted to remove at least one substance from the water.

14. The process according to claim 13, wherein the treating material is adapted remove one or more substances selected from the group consisting of heavy metals, organics, halogenated organics, polyaromatics or halogenated polyaromatics.

15. The process according to claim 14, wherein the heavy metal is selected from the group consisting of lead, nickel, mercury, copper or arsenic.

* * * * *